United States Patent [19]

Schiehser et al.

[11] Patent Number: 5,468,774

[45] Date of Patent: Nov. 21, 1995

[54] TETRONIC, THIOTETRONIC AND TETRAMIC ACID DERIVATIVES AS PHOSPHOLIPASE A2 INHIBITORS

[75] Inventors: Guy A. Schiehser, Yardley, Pa.; Craig E. Caufield; Nancie A. Senko, both of Plainsboro, N.J.; Gregory F. VonBurg, Princeton, N.J.

[73] Assignee: American Home Products Corporation, Madison, N.J.

[21] Appl. No.: 403,318

[22] Filed: Mar. 14, 1995

Related U.S. Application Data

[62] Division of Ser. No. 303,096, Sep. 8, 1994, abandoned, which is a division of Ser. No. 71,627, Jun. 3, 1993, Pat. No. 5,366,993, which is a continuation-in-part of Ser. No. 874,928, Apr. 28, 1992, abandoned.

[51] Int. Cl.$^6$ .................... A61K 31/34; C07D 307/46
[52] U.S. Cl. .................... 514/471; 514/473; 549/318
[58] Field of Search .................... 549/318; 514/473, 514/471

[56] References Cited

U.S. PATENT DOCUMENTS

| 4,874,782 | 10/1989 | Bonjouklian et al. | 549/313 X |
|---|---|---|---|
| 5,366,993 | 11/1994 | Schiehser et al. | 514/445 |

FOREIGN PATENT DOCUMENTS

| 49-69659 | 7/1974 | Japan | 549/318 |
|---|---|---|---|
| 51-1633 | 1/1976 | Japan | 549/318 |
| 62-019582 | 1/1987 | Japan . | |
| 1276061 | 6/1972 | United Kingdom | 549/318 |

OTHER PUBLICATIONS

Nomura, et al., Chem. Bull. Pharm., 34(12); pp. 5188–5190 (1986).
Tanaka, et al., Chem. Bull. Pharm., 27(8); pp. 1901–1906 (1978).

Primary Examiner—Joseph Paul Brust
Attorney, Agent, or Firm—Steven R. Eck

[57] ABSTRACT

There are disclosed compounds of the formula:

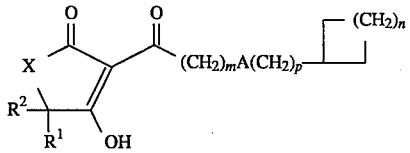

wherein
  X is O;
  $R^1$ and $R^2$ are each, independently, hydrogen, $C_1$–$C_{10}$ alkyl, $C_3$–$C_{20}$ cycloalkyl, phenylloweralkyl, or substituted phenylloweralkyl substituted by halo, lower alkyl, lower alkoxy, halo lower alkyl, amino, monoloweralkylamino, diloweralkylamino or sulfonamido;
  A is O, S, NR, or a chemical bond;
  R, if present, is hydrogen or loweralkyl;
  m is 0–15;
  n is 3–12;
  p is 0–15,
  where m+p=2–15;
and the pharmacologically acceptable salts thereof. Also disclosed is a method for treating immunoimmflammatory conditions in mammals which comprises administering to a mammal so afflicted an effective amount of a compound having the formula above wherein X, $R^1$, $R^2$, A, R, if present, m and p are as listed above and n=3–12 and m+p=2–15.

12 Claims, No Drawings

TETRONIC, THIOTETRONIC AND TETRAMIC ACID DERIVATIVES AS PHOSPHOLIPASE A2 INHIBITORS

This application is a division of U.S. Ser. No. 08/303,096, filed Sep. 8, 1994, now abandoned, which was a division of co-pending application U.S. Ser. No. 08/071,627, filed Jun. 3, 1993, which issued as U.S. Pat. No. 5,366,993 and which is a continuation-in-part of U.S. Ser. No. 07/874,928, filed Apr. 28, 1992, now abandoned.

The present invention is directed to certain tetronic acid derivatives having anti-inflammatory activity and to a method for using them as anti-inflammatory agents.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. These endoperoxides are also the precursors of the thromboxanes $(Tx)A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99,743 (1980). Cyclooxygenase metabolites are known to participate directly in the inflammatory response [see Higgs et al., Annals of Clinical Research, 16, 287–299 (1984)]. This is through their vasodepressor activities, participation in pain and fever and augmentation of peptide mediator vascular permeability and edema forming properties. Finally, various aspects of cell mediated immunity are influenced by cyclooxygenase products.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.*, 215, 115–118 (1980); *Biochem. Biophys. Res. Commun.*, 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature*, 288,484–486 (1980)], and another leukotriene, $LTB_4$, is a powerful chemotactic factor for leukocytes [see A. W. Ford-Hutchinson, *J. Roy. Soc. Med.*,74, 831–833 (1981)]. The activity of leukotrienes and slow-reacting substances as mediators of inflammation and hypersensitivity is extensively reviewed in Bailey and Casey, *Ann. Reports Med. Chem.*, 17, 203–217 (1982).

Phospholipase $A_2$ ($PLA_2$) is the critical rate limiting enzyme in the arachidonic acid (AA) cascade since it is responsible for the hydrolysis of esterified AA from the C-2 position of membrane phospholipids. This reaction generates two products (1) free AA which is then available for subsequent metabolism by either the cyclooxygenase or lipoxygenase enzymes and (2) lysophospholipid. When alkylarachidonyl-glycerophosphatidylcholine is acted upon by the $PLA_2$ the generation of platelet activating factor (PAF) is initiated; PAF is pro-inflammatory in its own right [see Wedmore et al., *Br. J. Pharmacol.*, 74, 916–917 (1981)]. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., *Nature*, London, 278, 456 (1979) and. Hirata et al., *Proc. Natn. Acad. Sci., U.S.A.*, 77, 2533 (1980)].

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the eicosanoids and/or PAF. Thus, while $PLA_2$ has been shown to be required for platelet aggregation [Pickett et al., *Biochem. J.*, 160, 405 (1976)], cardiac contraction and excitation [Geisler et al., *Pharm. Res. Commun,*, 9, 117 (1977)], as well as prostaglandin synthesis [Vogt, *Adv. Prostagl. Throm. Res.*, 3, 89 (1978)], the inhibition of $PLA_2$ is indicated in the therapeutic treatment of both PAF induced or cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation, as well as in the modulation of PAF-mediated biological processes, such as embryonic implantation, thus making the compounds useful as anti-fertility agents.

The invention provides novel compounds of the formula

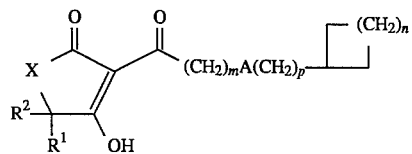

wherein

X is O;

R is hydrogen or lower alkyl;

$R^1$ and $R^2$ are each, independently, hydrogen, $C_1$–$C_{10}$ alkyl, $C_3$–$C_{20}$ cycloalkyl, phenylloweralkyl, or phenylloweralkyl substituted by halo, lower alkyl, lower alkoxy, halo lower alkyl, amino, monoloweralkylamino, diloweralkylamino or sulfonamido;

A is O, S, NR, or a chemical bond;

m is 0–15;

n is 3–12;

p is 0–15 ,wherein m+p=2–15;

and the pharmacologically acceptable salts thereof.

The invention further provides a method for treating immunoinflammatory conditions such as allergy, anaphylaxis, asthma, inflammatory bowel disease, endotoxic shock, dermatitis and psoriasis, in mammals, which comprises administering to a mammal so afflicted an effective amount of a compound having the formula

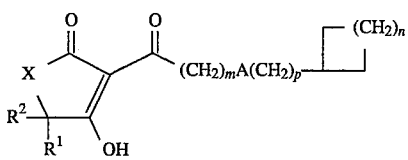

wherein

X is O;

$R^1$ and $R^2$ are each, independently, hydrogen, $C_1$–$C_{10}$ alkyl, $C_3$–$C_{20}$ cycloalkyl, phenylloweralkyl, or substituted phenylloweralkyl substituted by halo, lower alkyl, lower alkoxy, halo lower alkyl, amino, monoloweralkylamino, diloweralkylamino or sulfonamido;

A is O, S, NR or a chemical bond;

R, if present, is hydrogen or loweralkyl;

m is 0–15;

n is 0–20;

p is 0–15, where m+p≦15;

and the pharmacologically acceptable salts thereof.

The terms "loweralkyl" and "lower alkoxy" when used alone or in combination, refer to moieties having 1–6 carbon atoms in the carbon chain. The term "halo" refers to fluoro, chloro, bromo or iodo.

It will also be understood by those skilled in the art that the structure:

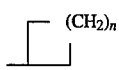

indicates an alkylene ring having 3+n carbon atoms, in cases where n=0, a cyclopropyl ring will be indicated. It will also be understood that, in cases where A is a chemical bond, a continual alkylene chain is indicated in which the number of carbon atoms in the chain is equal to m plus p. Therefore, in the compound genus listed above, m plus p will be equal to from 2 to 15 carbon atoms, i.e. if one of m or p is zero, the other must be at least two such that m+p equals from 2 to 15 carbon atoms. For the method of treatment disclosed herein, though, m and p may be from 0–15 carbon atoms and m+p may be ≦15.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic. The compounds of the invention are capable of forming alkali metal and alkaline earth salts and salts of pharmacologically acceptable cations derived from ammonia or a basic amine. Examples of the latter include but are not limited to cations such as ammonium, mono-, di-, and trimethylammonium, mono-, di-, and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

The compounds within the scope of the invention by virtue of their configuration, exhibit stereoisomerism. Accordingly, the compounds of the invention include the diastereomers, enantiomorphs, racemates and mixtures thereof.

The compounds within the scope of the invention can be prepared by a variety of synthetic routes using conventional methods. According to one preparative scheme, a suitable cycloalkyl alcohol is oxidized to the corresponding aldehyde, which is treated with a Wittig reagent to provide an unsaturated ester, which in turn is reduced to the saturated ester, the latter being hydrolyzed to the free acid:

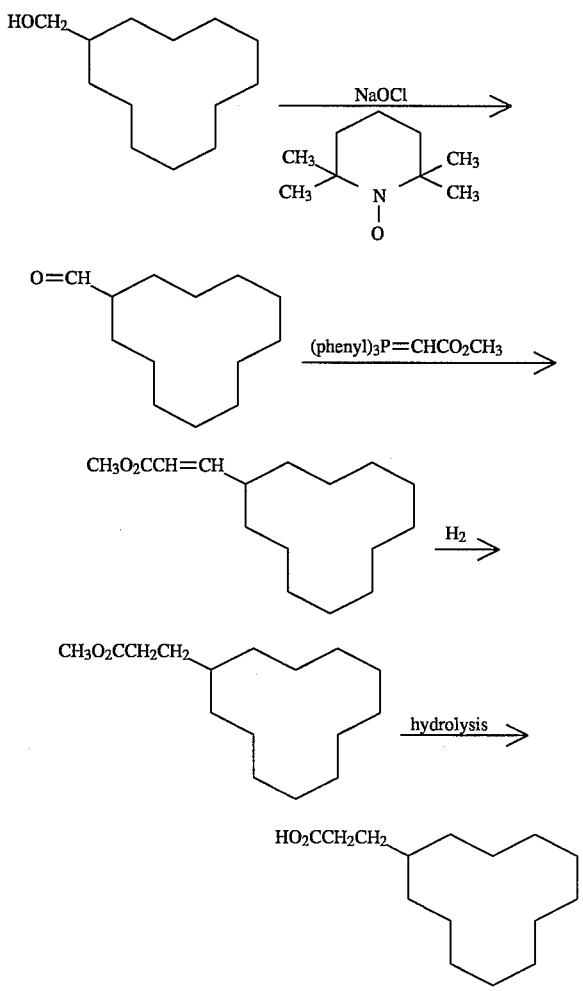

The intermediate free acid is then reacted with a tetronic, tetramic or thiotetronic acid to yield the desired final product:

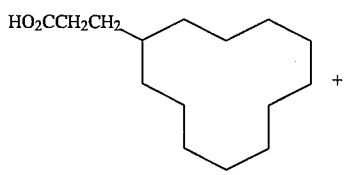

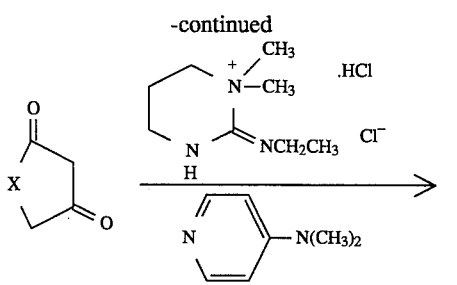

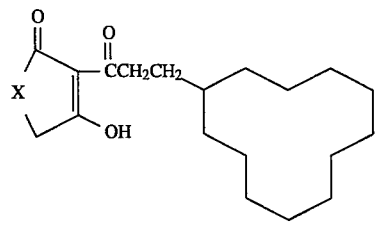

In an alternative sequence, a cycloalkyl ketone is methylenated to give a epoxide which rearranges under acidic conditions to yield an aldehyde:

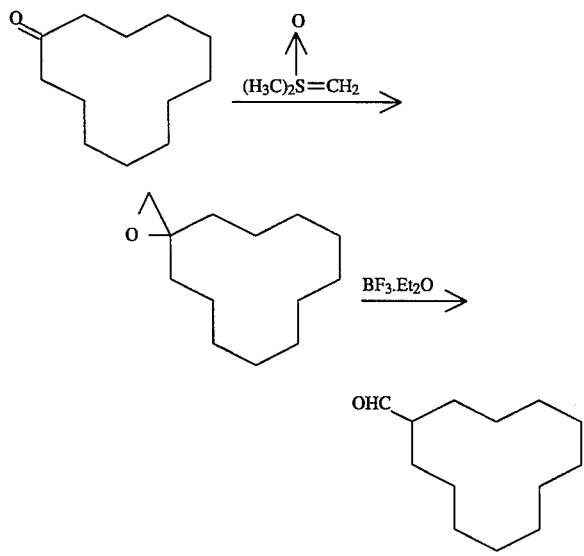

The carboxylic acid starting materials (used to make the acylated tetronic and thiotetronic acids) in which A=O or S, can be prepared by starting with an available lipid aldehyde or ester and reducing this compound to the alcohol as shown below.

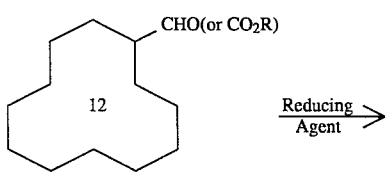

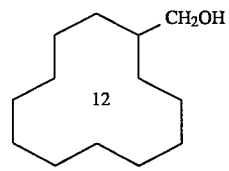

To form compounds of this invention where A=O, the alcohol, when reacted with a suitable base such as sodium hydride to form the salt, is then reacted with a suitable electrophile such as allyl bromide to give the allyl ether or with tert-butylbromoacetate to give the alkylated t-butyl ester. The tert-butyl ester can be cleaved to the acid under acidic conditions. In the case of the allyl ether, this compound must be oxidatively cleaved ($O_3$ or $OsO_4/NaIO_4$) to give the aldehyde which is further oxidized to the acid using Jones reagent or $KMnO_4$. See below.

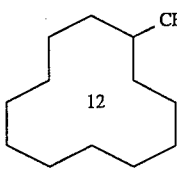

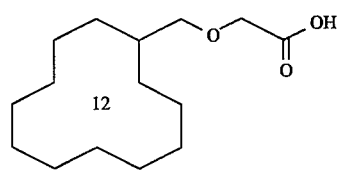

To form compounds of this invention where A=S, the alcohol (see above), is converted to a suitable leaving group (Br with $CBr_4/PPh_3$; OMs with $MsCl/Et_3N$, OTs with TsCl/pyridine) which is then reacted with an alkyl thioglycolate salt to give the alkylated ester which can be cleaved to the acid under saponifying conditions (base, water).

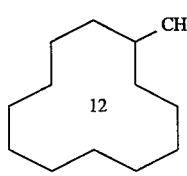

To form compound of this invention where A=NR, the isocyanate is prepared from a suitable lipid acid by converting to the acid chloride, reaction with TMS azide to give the acylazide. This acyl azide smoothly converts to the isocyanate by heating. This isocyanate is then reacted with tetronic or thiotetronic acid to form the compounds of this invention.

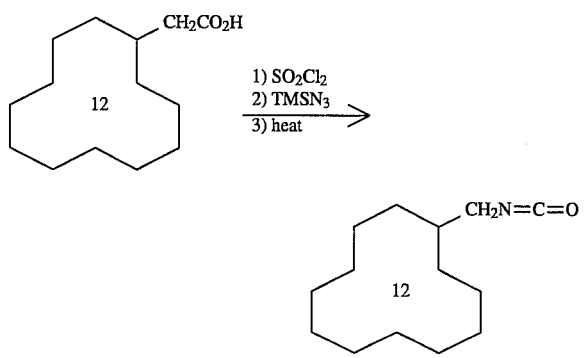

The aldehyde is then subjected to olefination with a tetronic, tetramic or thiotetronic acid phosphonate, followed by hydrogenation to yield the desired final product:

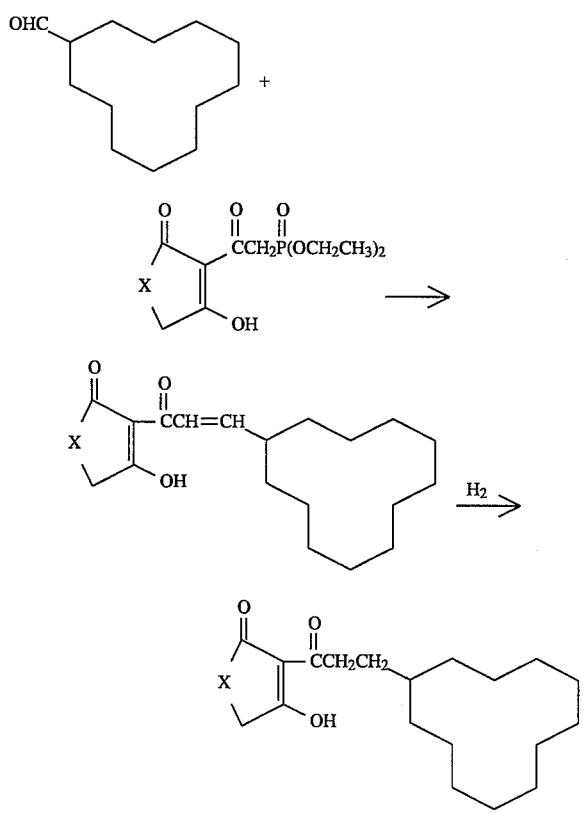

The starting materials in the above preparative sequences are all commercially available or can be prepared by conventional methods as taught in the chemical literature.

The compounds of the invention, by virtue of their ability to inhibit activity of $PLA_2$ enzyme, are useful in the treatment of conditions mediated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; and various inflammatory conditions such as those present in rheumatoid arthritis, osteoarthritis, tendinitis, bursiris, psoriasis (and related skin inflammation), uveitis, and the like.

When the compounds within the scope of the invention are employed in the treatment of allergic airways disorders or in anti-inflammatory therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be used topically and for this purpose they may be formulated in the form of dusting powders, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The standard pharmacological procedures, which are described fully in the examples given hereafter, inter alia, determine the specificity of action of the compounds of the invention as $PLA_2$ inhibitors as measured by their ability to inhibit platelet-activating factor and $LTB_4$ biosynthesis in human neutrophils; by their ability to inhibit arachidonic acid release mediated by human and non-human source $PLA_2$, and by pharmacological testing which demonstrates the ability of the compounds of the invention to inhibit the lipoxygenase and cyclooxygenase pathways of arachidonic acid metabolism.

The following examples show the preparation and pharmacological testing of compounds within the invention.

EXAMPLE 1

3-(3-Cyclododecyl-1-oxopropyl)-4-hydroxy-2(5H)-furanone

A. Cyclododecanecarboxaldehyde

To a solution of 9.92 g (50 mmol) of cyclododecane methanol in 100 ml of methylene chloride under a nitrogen atmosphere is added 50 mg of 2,2,6,6 -tetramethyl-1-piperidinyloxy, free radical (TEMPO) and 510 mg (5 mmol) of sodium bromide in 5 ml of water. The solution is cooled to 10°–15° C. and a solution of 100 ml of 5.25% aqueous sodium hypochlorite and 2.0 g of sodium bicarbonate is added over 1 hour. The reaction mixture is allowed to warm to room temperature and after 1 hour is diluted with methylene chloride. The organic phase is washed with aqueous sodium thiosulfate, aqueous bicarbonate and water. The methylene chloride layer is dried over magnesium sulfate, filtered and evaporated in vacuo to give 9.43 g of crude title compound as an oil: IR (film) 1723 cm$^{-1}$; NMR (CDCl$_3$)) δ 1.34 (bs, 18 H), 1.41 (m, 4 H), 1.54 (m, 2 H), 1.65 (m, 2 H), 2.40 (m, 1 H), 9.64 (d, 1 H, J=1.6 Hz) M$^+$ (EI) 196

B. 3-Cyclododecylprop-2-enoic acid, methyl ester

To a solution of 9.4 g (48 mmol) of cyclododecanecarboxaldehyde in 100 ml of toluene is added 16.0 g (48 mmol) of methyl triphenylphosphoranylidene acetate. The mixture is heated to reflux and is maintained under a nitrogen atmosphere for 21 hours. The solution is removed of solvent in vacuo and is triturated with ethyl ether to give 10.8 g of white solid and a filtrate which gives an oily solid upon evaporation. The latter material is triturated with ethyl ether and filtered to give on evaporation of the filtrate, 13.7 g of crude title compound: IR (film) 1722 cm$^{-1}$; NMR (CDCl$_3$) δ 1.36 (bs, 18 H), 1.53 (m, 4 H), 2.35 (m, 1 H), 3.73 (s, 3 H), 5.78 (dd, 1H, J=1, 16 Hz), 6.88 (dd, 1 H, J=8, 16 Hz).

Anal. Calc'd. for C$_{16}$H$_{28}$O$_2$: C, 76.14; H, 11.18

Found: C, 75.82; H, 9.62

C. 3-Cyclododecylpropanoic acid, methyl ester

To a solution of 12.6 g (50 mmol) of methyl 3-cyclododecylprop-2-enoate in 100 ml of methanol is added 3.6 g (150 mmol), 3 equiv) of magnesium metal (activated by prior heating to 160° C.) and the mixture is stirred at room temperature for 2 hours (ice bath cooling is applied when necessary to control exothermic excursions). The reaction mixture is digested with ice cold 2N hydrochloric acid and is extracted with ethyl ether (3 times). The combined ethereal extracts are washed with 2N hydrochloric acid and are dried over magnesium sulfate. Filtration and evaporation gives an oily solid. Flash chromatography on silica gel using hexane/ethyl ether (10:1) as eluting solvent affords 7.80 g of the title compound: IR 1748 cm$^{-1}$; NMR (CDCl$_3$) δ 1.33 (m, 23 H), 1.54 (t, 2 H, J=8 Hz), 2.31 (t, 2 H, J=8 Hz), 3.66 (s, 3H).

Anal. Calc'd. for C$_{16}$H$_{30}$O$_2$: C, 75.54; H, 11.89

Found: C, 75.67; H, 10.52

D. 3-Cyclododecylpropanoic acid

To a solution of 7.6 g (30 mmol) of methyl 3-cyclododecylpropanoate in 100 ml of methanol is added 2.4 g of sodium hydroxide. The mixture is heated to 55° C. and is maintained for 4 hours. The reaction mixture is diluted with water and is extracted with hexane. The aqueous phase is acidified with 1N hydrochloric acid and is extracted (2 times) with ethyl ether. The combined ethereal extracts are washed with 1N hydrochloric acid and are dried over magnesium sulfate. Filtration and evaporation gives 7.48 g of crude title compound. Recrystallization of a portion of the product from hexane gives 1.81 g of the title compound: m.p. 72°–74° C.; IR (KBr) 1715 cm$^{-1}$; NMR (CDCl$_3$) δ 1.34 (m, 23 H), 1.57 (q, 2 H, J=8 Hz), 2.36 (t, 2 H, J=8 Hz).

Anal. Calc'd. for C$_{15}$H$_{28}$O$_2$: C, 74.95; H, 11.74

Found: C, 74.90; H, 11.20

E. 3-(3-Cyclododecyl-1-oxopropyl)4-hydroxy-2(5H)-furanone

To a solution of 0.70 g (7 mmol) of tetronic acid in 20 ml of dry dimethylformamide at 0° C. is added 1.1 ml (836 mg, 8.3 mmol) of triethylamine and 0.31 g (2.5 mmol) of dimethylaminopyridine. After stirring for 5 minutes, 2.0 g (8.3 mmol) of 3-cyclododecylpropanoic acid is added followed by 1.6 g (8.3 mmol) of 1-( 3-dimethylaminopropyl)-3-ethylcarbodiimide hydrochloride. After 10 minutes the ice bath is removed and the reaction mixture is allowed to stir overnight at room temperature. The reaction mixture is then poured into 1.0N hydrochloric acid and extracted 3 times with ethyl acetate. The organic layers are combined, washed with brine, dried over magnesium sulfate, filtered and concentrated to give a yellow oil. The oil is subjected to flash chromatography using acidic silica gel and hexane/ethyl acetate (3:2) as the mobile phase to give an off white solid: m.p. 99°–102° C.; IR (KBr) 2940, 1710, 1600 and 1470 cm$^{-1}$; NMR (CDCl$_3$) (mixture of tautomeric forms) δ 1.34 (mc, 22 H), 1.50 (bs, 1 H), 1.61 (m, 2 H), 2.92 (m, 2 H), 4.55 and 4.70 (s, 2 H); MS (EI) 322.

Anal. Calc'd. for C$_{19}$H$_{30}$O$_4$: C, 67.87; H, 5.70

Found: C, 67.62; H, 5.98

EXAMPLE 2

3-(3-cyclododecyl-1-oxopropyl)-4-hydroxy-2(5H)-thiophenone

To a solution of 0.80 g of thiotetronic acid in 20 ml of dry dimethylformamide at 0° C. is added 1.1 ml (836 mg, 8.3 mmol) of triethylamine and 0.31 g (2.5 mmol) of dimethylaminopyridine. After stirring for 5 minutes, 2.0 g (8.3 mmol) of 3-cyclododecylpropanoic acid is added followed by 1.6 g (8.3 mmol) of 1-( 3-dimethylaminopropyl)-3-ethyl carbodiimide hydrochloride. After 10 minutes the ice bath is removed and the reaction mixture is allowed to stir overnight at room temperature. The reaction mixture is then poured into 1N hydrochloric acid and extracted 3 times with ethyl acetate. The organic layers are combined, washed with brine, filtered and evaporated to give a brown oil. The oil is subjected to flash chromatography using acidic silica gel and hexane/ethyl acetate (9:1) as the mobile phase to give an off white solid: m.p. 60°–62° C.; IR (KBr) 2940, 1700, 1630, and 1590 cm$^{-1}$: NMR (CDCl$_3$) δ 1.33 (bs, 22 H), 1.49 (bs, 1 H), 1.58 (m, 2 H), 2.96 (m, 2H), 3.77 and 3.98 (singlets, 2 H); MS (EI) M+ 338.

Anal. Calc'd. for C$_{19}$H$_{30}$O$_3$S: C, 67.87; H, 5.70

Found: C, 67.62; H, 5.98

EXAMPLE 3

3-(3-cyclododecyl-1-oxopropyl)-1.5-dihydro-4-hydroxy-1-methyl-1H-pyrrolin-2-one

A. 1-Oxaspiro[2.11]tetradecane

To a dry flask under nitrogen is added 3.1 g (64.6 mmol) of 50% sodium hydride in mineral oil. The sodium hydride is washed twice with hexanes, is suspended in 80 ml of dry dimethyl sulfoxide and then 14.3 g (65.0 mmol) of trimethylsulfoxonium iodide is added. The mixture is stirred at room temperature for several hours and then 11.8 g (64.7 mmol) of cyclododecanone is introduced. The mixture is allowed to stir overnight at room temperature and then is heated for 1 hour at 50° C. The mixture is cooled to room temperature, is dissolved in 500 ml of cold water and is extracted seven times with ethyl ether. The combined organic layers are washed once with water, dried over magnesium sulfate and subjected to evaporation in vacuo. The residue is chromatographed on silica gel using 20% ethyl acetate/hexanes as the mobile phase to give 10 g (78%) of the title compound as a colorless oil: NMR (CDCl$_3$) δ 1.2–1.8 (m, 18 H), 2.05 (s, 1H), 2.4 (t, 2 H, J=5.0 Hz), 2.45 (d, 2H), 2.58 (s, 2 H).

B. Cyclododecanecarboxaldehyde

To 5.0 g (25.5 mmol) of 1-oxaspiro[2.11]tetradecane in 50 ml of dry ether at 0° C. is slowly added 1.8 ml (2.1 g, 14.6 mmol) of boron trifluoride etherate. The ice bath is removed and after 15 minutes at room temperature the solution is partitioned between ether and saturated sodium bicarbonate. The organic phase is evaporated to give a clear oil. Flash chromatography over silica gel using a hexane to hexane-:ethyl acetate (9:1) gradient give 1.6 g (34%) of a clear oil: NMR (CDCl$_3$) δ 1.28–1.8 (m, 18 H), 2.03 (s, 1 H), 2.42 (m, 1 H), 9.62 (s, 1 H)

C. Sarcosine, N-(4-bromo-1,3-dioxo)butane, ethyl ester

To 38 ml (40.8 g, 486 mmol) of diketene in 200 ml of dry methylene chloride at −78° C. is slowly added 24.0 ml (75 g, 468 mmol) of bromine. After stirring at −78° C. for 1 hour, the mixture is subjected to the addition of 90 ml (65.3 g, 647 mmol) of triethylamine followed by 50 g (326 mmol) of sarcosine ethyl ester hydrochloride. After stirring at −78° C. for 2 hours no starting materials are evident by thin layer chromatography. The mixture is taken up in water and the methylene chloride phase is removed. The organic layer is dried over magnesium sulfate and evaporated to give a black residue which is subjected to flash chromatography on silica gel using hexanes/ethyl acetate (3:2) to give 23.1 g of the title compound as a crude red oil which is used without further purification.

D. [2-(1.5-Dihydro-4-hydroxy-1-methyl-2-oxo-1H-pyrrol-3-yl)-2-oxoethyl]-phosphonic acid, diethyl ester To 28.0 g (250 mmol) of potassium t-butoxide in 40 ml of dimethylformanaide at 0° C. is slowly added 29 ml (31 g, 225 mmol) of diethyl phosphite. The mixture is stirred for 45 minutes and 20.0 g (75.2 mmol) of sarcosine, N-(4-bromo-1,3-dioxo)butane ethyl ester in 20 ml of dry tetrahydrofuran is added. After the addition is complete, the mixture is allowed to stir at room temperature overnight. Thin-layer chromatography using phosphoric acid-treated plates indicates the consumption of starting material. The mixture is acidified with 1N hydrochloric acid and is extracted three times with dichloromethane. The combined organic layers are taken up in 1N sodium hydroxide, washed with dichloromethane, reacidified and then washed three times with dichloromethane. The combined organic layers are dried over magnesium sulfate and evaporated to give 19.17 g (88%) of a dark oil: NMR (CDCl$_3$) δ 1.35 (t, 4H, J=7 Hz), 2.9 (s, 2 H), 2.97 (s, 2 H), 3.05 (s, 2 H), 3.6 (d, 1 H, J= 25 Hz), 3.8 (s, 1 H), 4.2 (m, 4 H), 8.0 (s, 1 H)

E. 3-(Cyclododecyl-1-oxo-2-propenyl)-1,5-dihydro-4-hydroxy-1-methyl-1H-pyrrol-2-one To a solution of 1.3 g (4.5 mmol) of diethyl [2-(1,5-dihydro-4 -hydroxy-1-methyl-2-oxo-1H-pyrrol-3-yl)-2-oxoethyl]phosphonate in dry tetrahydrofuran at 0° C. is slowly added 1.0 g (8.9 mmol) of potassium t-butoxide in 20 ml of dry tetrahydrofuran. After 0.5 hour at 0° C., 0.8 g (4.1 mmol) of cyclododecanecarboxaldehyde is added and the reaction mixture is allowed to stir overnight at room temperature. The mixture is evaporated under reduced pressure and the residue is dissolved in 1N sodium hydroxide, washed once with dichloromethane, and acidified with concentrated hydrochloric acid. The acidified aqueous phase is extracted four times with dichloromethane and the combined organic phases are dried over magnesium sulfate and evaporated in vacuo. The residue is chromatographed using acidic silica gel and hexane:ethyl acetate (3:1) to give 0.56 g (35%) of an off white solid: NMR (CDCl$_3$) δ 2.2–2.7 (bs, 22 H), 2.45 (m, 2 H), 3.0 (s, 3 H), 3.81 (s, 2 H), 7.1 (s, 2H).

F. 3-(3-Cyclododecyl-1-oxopropyl)-1,5-dihydro-4-hydroxy-1-methyl-1H-pyrrolin-2-one To 0.56 g (1.7 mmol) of 3-(3-cyclododecyl-1-oxo-2-propenyl)-1,5 -dihydro-4-hydroxy-1-methyl-1H-pyrrol-2-one in 20 ml of ethyl acetate is added a catalytic amount of 10% palladium on carbon. The mixture is allowed to stir at room temperature for 5 hours after which time no starting material is evident by thin layer chromatography. The mixture is passed through a Celite pad and is evaporated in vacuo. The residue is chromatographed over acid-treated silica gel using hexane/ethyl acetate (2:1) to give 0.45 g of a white solid: m.p. 66°–68° C.; IR (KBr) 2820, 2660, 1720, 1650, 1600 cm$^{-1}$; NMR (CDCl$_3$) δ 1.28 (bs, 22 H), 1.44 (bs, 1 H), 1.51 (m, H), 2.78 and 2.88 (triplets, 2 H, J=8 Hz), 2.95 and 2.97 (singlets, 3 H, 1:5), 3.66 and 3.79 (s, 2 H, 7:1); MS M+335.

Anal. Calc'd. for C$_{20}$H$_{33}$NO$_4$: C, 71.60; H, 9.91, N, 4.17
Found: C, 71.23; H, 9.64; N, 4.14

EXAMPLE 4

3-(3-cyclododecyl-1-oxopropyl)-4-hydroxy-2(5H)-thiophenone compound with 2-amino-2-(hydroxymethyl-1,3-propanediol (1:1)

To 2.5 g (74 mmol) of 3-(3-cyclododecyl-1-oxopropyl)-4-hydroxy( 5H)thiophenone in 20 mL of ethanol at 70° C. is added 0.85 g (7.0 mmol) of trishydroxymethylaminomethane dissolved in 5 mL of water. The reaction mixture is stirred at 70° C. for 0.5 hours and then the solvents are evaporated. The residue is recrystallized from tetrahydrofuran/isopropyl ether (2:1) to give 1.3 g of a white solid: m.p. 164°–166° C.; IR (KBr) 2860–3460, 1640, 1580 cm$^{-1}$; NMR (DMSO-d$_6$)δ 1.2–1.4 (m, 10H), 2.55 (t, 2H, J=7 Hz), 3.25 (s, 2H), 3.3 (s, 6H), 3.47 (d, 6H, J=5 Hz), 5.15 (t, 3H, J=5 Hz), 7.6 ppm (bs, 3H); MS ((+)FAB): [M-Base+2H] 339.

Anal. Calc'd. for C$_{23}$H$_{41}$NO$_6$S: C, 60.1; H, 8.99; N, 3.05
Found: C, 59.82; H, 8.74; N, 3.77

EXAMPLE 5

3-(4-cyclododecyl-1-oxobutyl)-4-hydroxy-2 (5H)-thiophenone

1-(3-phenyl-1-propenyl)cyclododecane

To 11.4 g (25.5 mmol) of phenylethyl triphenylphosphonium bromide in 50 mL of dry ether at 0° C. is added 10.2 mL (25.5 mmol) of 2.5M butyllithium. The suspension is stirred at 0° C. for 1 hour followed by the addition of 5.0 g (25.5 mmol) of cyclododecane carboxaldehyde. The mixture is stirred at room temperature for 3 hours after which time no starting material is evident by TLC. The reaction mixture is quenched with 1N HCl. The layers are separated and the aqueous layer is washed twice with ethyl ether. The combined organic layers are dried over a MgSO$_4$ and the ether is evaporated. The residue is flash chromatographed on silica gel using hexanes to give 6.4 g of a colorless oil: NMR (CDCl$_3$) δ 1.0–1.6 (m, 10H), 2.6 (m, 1H), 3.4 (d, 2H, J=8 Hz,), 5.3 (t, 1H, J=7 Hz), 5.45 (q, 1H, J=7 Hz), 7.2 ppm (m, 5

B. 1-(3-phenylpropyl)cyclododecane

To 6.4 g (22.5 mmoles) of 1-(3-phenyl-1-propenyl)cyclododecane in 50 mL of ethanol is added 0.48 g of 10% palladium on carbon. The reaction mixture is subjected to hydrogen (50 psi) atmosphere using a Paar hydrogenator and shaken overnight after which time no starting material is evident by TLC. The reaction mixture is filtered through Celite which is washed with additional ethanol. The filtrate is evaporated and the crude residue (5.8 g) is used directly for the next step: NMR (CDCl$_3$) δ 1.2–1.4 (m, 10H), 1.6 (m, 2H), 2.55 (t, 2H, J=8 Hz), 7.2 (m, 5H).

C. 4-cyclododecylbutanoic acid

To a flask containing 90 mL of water, 60 mL of acetonitrile and 60 mL of carbon tetrachloride is added 4.8 g (16.8 mmol) of 1-(3-phenylpropyl)cyclododecane, 50.0 g (0.25 mol) of sodium periodate and then 70 mg (0.3 mmol) of ruthenium trichloride hydrate. The reaction mixture is allowed to stir at room temperature overnight. The mixture is then taken up in dichloromethane and 1N HCl and the layers separated. The aqueous phase is washed 3 times with dichloromethane and the combined organic layers are dried over MgSO$_4$ and the solvents evaporated. The residue is taken up in ether, filtered through Celite and the filtrate evaporated. The crude product is flash chromatographed using acidic silica gel and 30% ethyl acetate/hexanes to give 3.25 g of a white solid: NMR (CDCl$_3$) δ 1.2–1.5 (m, 10H), 1.65 (m, 2H), 2.35 (t, 2H, J=8 Hz).

D. 3-(4-cyclododecyl-1-oxobutyl)-4-hydroxy-2-(5H)thiophenone

To a dry flask under N$_2$ atmosphere at 0° C. is added 1.31 g (11.3 mmol) of thiotetronic acid in 40 mL of dry dichloromethane followed by 1.42 mL (10.2 mmol) of triethylamine and 0.38 g (3.1 mmol) of 4-dimethylaminopyridine. After stirring at 0° C. for 5 minutes, 2.6 g (10.2 mmol) of cyclododecylbutanoic acid is added, followed by 4.8 g (11.3 mmol) of 1-cyclohexyl-3-(2-morpholinoethyl) carbodiimide metho p-toluenesulfonate. After stirring for 10 minutes, the reaction mixture is allowed to warm to room temperature and is stirred overnight. The reaction mixture is quenched with 1N HCl. The layers are separated and the aqueous phase is washed once with dichloromethane. The combined organic layers are washed twice with aqueous sodium bicarbonate and twice with aqueous 2N HCl. The organic phase is then dried over MgSO$_4$ and the dichloromethane evaporated. The residue is flash chromatographed on acidic silica gel using 8% ether/hexanes, dissolved in ether, washed with 1N HCl, dried and evaporated to give 1.2 g of a white solid: m.p. 62°–69° C.; IR; NMR (CDCl$_3$) δ 1.2–1.4 (m, 10H), 1.5 (s, 4H), 1.65 (m, 2H), 2.9 (t, 2H, J=7 Hz), 3.96 (s, 2H); MS.

Anal. Calc'd. for C$_{20}$H$_{32}$O$_3$S: C, 68.53; H, 8.63
Found: C, 67.72; H, 8.84

EXAMPLE 6

3-(4-cyclododecyl-1-oxobutyl)-4-hydroxy-2(5H)-thiophenone compound with 2-amino-2-hydroxymethyl)-1,3-propanediol (1:1)

To 0.8 g (2.3 mmol) of 3-(4-cyclododecyl-1-oxobutyl)-4-hydroxy-2-(5H)thiophenone in 20 mL of ethanol at 70° C. is added 0.26 g (2.2 mmol) of trishydroxymethyl aminomethane dissolved in 5 mL of water. The reaction mixture is stirred at 70° C. for 0.5 hours and then the solvents are evaporated. The residue is recrystallized from tetrahydrofuran/ether (2:1) to give 0.66 g of an off white solid: m.p. 141°–144° C.; IR (KBr) 3420, 2920, 2830, 1580 cm$^{-1}$; NMR (DMSO-d$_6$) δ 1.1–1.4 (m, 10H), 2.55 (t, J=7 Hz, 2H), 3.26 (s, 1H), 3.31 (s, 4H), 3.47 (d, J=5, 3 Hz), 5.15 (t, J=5 Hz, 2H), 7.6 (bs, 2H); MS (DCI) [M+H]$^+$ 353.

Anal. Calc'd. for C$_4$H$_{43}$NO$_6$S: C 60.86; H 9.15; N, 2.96
Found: C, 60.91; H 9.16; N, 2.88

EXAMPLE 7A

Cyclododecylene acetic acid

A solution of 12 mL of dicyclohexylamine (60.4 mmol) in 100 mL of dry THF was subjected to the addition of 24.2 mL of 2.5M in butyl lithium (60.4 mmol) at −78° C. After 15 minutes, 11.1 mL of ethyl trimethylsilyl acetate (60.4 mmol) was added dropwise and after another 15 minutes, 5.5 g of cyclododecanone (30.2 mmol) in dry THF was added dropwise. After stirring at 78° C. for 1 h, the reaction mixture was allowed to warm to room temperature. 1.2 g of sodium bisulfate monohydrate was added and the reaction mixture was stirred for another 15 minutes. It was quenched with saturated NH$_4$Cl followed by 1N HCl. The phases were separated, the aqueous layer washed with ether. The combined organic layers were washed with brine, dried over MgSO$_4$ and evaporated to give 6.0 g of a tan oil (79%).

EXAMPLE 7B

Ethyl cyclodecyl acetate

To 6.0 g of ethyl cyclodecylane acetate (23.8 mmol) in 150 mL of methanol was added 3.0 g (119 mmol) of magnesium turnings. The reaction mixture was stirred at room temperature overnight, after which time, all the magnesium had been consumed. The reaction was quenched with 3N HCl and extracted with ether. The combined ether layers were dried over MgSO$_4$ and evaporated to give 5.5 g of a tan oil (92%).

EXAMPLE 7C

Cyclododecyl acetic acid

To a solution of 1.73 g of sodium hydroxide (43.3 mmol) in water was added 5.5 g of ethyl cyclododecyl acetate in methanol. Water and THF were added until the solution was homogeneous. The reaction mixture was heated to 50° C. for several hours, the solvents stripped and the residue was partitioned between ether and 0.5N sodium hydroxide. The aqueous phase was acidified and extracted 3x with ether. The ether phases were combined, washed with brine, dried over MgSO$_4$ and evaporated to give 2.8 g of a white solid.

EXAMPLE 7D 3-(2-cyclododecyl-1-oxoethyl)-4-hydroxy-2(5H)-furanone

To a dry flask under N$_2$ atmosphere at 0° C. is added 1.46 g (14.6 mmol) of tetronic acid in 40 mL of dry dichloromethane followed by 1.85 mL (13.3 mmol) of triethylamine and 0.49 g (4.0 mmol) of 4-dimethylaminopyridine. After stirring at 0° C. for 5 minutes, 3.0 g (13.3 mmoles) of cyclododecyl acetic acid is added followed by 6.12 g (14.6 mmol) of 1-cyclohexyl-3-(2-morpholinoethyl) carbodiimide metho p-toluene sulfonate. After stirring for 10 minutes, the reaction mixture is allowed to warm to room temperature and stirred overnight. The reaction mixture is quenched with 1N HCl. The layers are separated and the aqueous phase is washed once with dichloromethane. The combined organic layers are washed twice with aqueous sodium bicarbonate and twice with aqueous 2N HCl. The organic phase is then dried over MgSO$_4$ and the dichloromethane evaporated. The residue is flash chromatographed on acidic silica gel using 90% ether/hexanes, taken up in ether, washed once with 1N HCl and recrystallized from cyclohexane to give 2.0 g of a light yellow solid: m.p. 133°–135° C.; IR (KBr) 2920 (C-H), 1770, 1650, 1600 cm$^{-1}$ (C=O); NMR (CDCl$_3$) δ 1.2–1.5 (m, 10H), 2.1 (m, 1H), 2.84 (d, 2H, J=7 Hz), 4.6 (bs, 2H), MS (EI) M$^+$ 308.

Anal. Calc'd. for C$_{18}$H$_{28}$O$_4$: C, 70.10; H, 9.15
Found: C, 70.38; H, 9.21

EXAMPLE 8

3-(2-cyclododecyl-1-oxoethyl)-4-hydroxy-2(5H)-thiophenone

To a dry flask under N$_2$ atmosphere at 0° C. is added 1.7 g (14.6 mmol) of thiotetronic acid in 40 mL of dry dichloromethane, followed by 1.85 mL (13.3 mmol) of triethylamine and 0.49 g (40 mmol) of 4-dimethylaminopyridine. After stirring at 0° C. for 5 minutes, 3.0 g (13.3 mmol) of cyclododecylacetic acid is added followed by 6.12 g (14.6 mmol) of 1-cyclohexyl-3-(2-morpholinoethyl)carbodiimide metho p-toluenesulfonate. After stirring for 10 minutes, the reaction mixture is allowed to warm to room temperature and stirred overnight. The reaction mixture is quenched with 1N HCl. The layers are separated and the aqueous layer is washed once with dichloromethane. The combined organic layers are washed twice with aqueous sodium bicarbonate and then twice with aqueous 2N HCl. The organic phase is then dried over MgSO$_4$ and the dichloromethane evaporated. The residue is flash chromatographed on acidic silica gel using 10% dichloromethane/hexanes, taken up in ether, washed once with 1N HCl and recrystallized from hexane to give 1.2 g of a white solid: m.p. 85°–87° C.; MS (EI) M$^+$ 324; IR (CHCl$_3$) 2930, 2860 (C-H), 1685, 1620, 1565 cm$^{-1}$; NMR (CDCl$_3$) δ 1.2–1.5 (m, 10H), 2.1 (m, 1H), 2.87 (d, 2H, J=7 Hz), 3.96 and 3.75 (s, 2H).

Anal. Calc'd. for C$_{18}$H$_{28}$O$_3$S: C, 66.63; H, 8.70
Found: C, 67.46; H, 8.81

EXAMPLE 9

3-(3-cyclohexyl-1-oxopropyl)-4-hydroxy-2(5H)-furanone

To a solution of 2.0 g of tetronic acid in 40 ml of dry N,N-dimethylformamide was added (at 0° C.) 3.1 ml of triethylamine and 0.81 g of dimethylaminopyridine. After stirring for 5 minutes, 3.4 ml of 3-cyclohexylpropanoic acid was added, followed by 4.6 g of 1-(3-dimethylaminopropyl)-3-ethyl carbodiimide hydrochloride. After 10 minutes the ice bath is removed and the mixture is allowed to stir overnight. The reaction mixture is quenched with 1N hydrochloric acid and the solution is washed 3 times with hexanes. The combined organic layers are combined, washed with brine, dried over magnesium sulfate and evaporated to give a yellow solid, which is recrystallized from hexanes to give light yellow crystals: m.p. 75°–78° C.; IR (KBr) 2910, 2820, 1750, 1640, 1600 cm$^{-1}$; NMR (CDCl$_3$) δ 0.9–1.8 (1 1H, m), 2.9 (t, 2H, J=6 Hz), 4.7 and 4.5 (s, 2H (tautomers)); MS EI M$^+$ 238.

Anal. Calc'd. for C$_{13}$H$_{18}$O$_4$: C, 65.53; H, 7.61
Found: C, 65.23; H, 7.74

EXAMPLE 10

3-(3-cyclohexyl-1-oxopropyl)-4-hydroxy-2(5H)-thiophenone

In the same manner as that described for Example 1 is prepared the title compound with the exception that thiotetronic acid is used instead of tetronic acid. Crystallization from hexanes gives yellow crystals: m.p.: 60°–62° C.; NMR (CDCl$_3$) δ 0.9–1.7 (m, 11H), 2.95 (t, 2H, J=8 Hz), 4.0 (s, 2H); IR 2920, 2840, 1680, 1560 cm$^{-1}$; MS (EI) M$^+$ 254.

Anal. Calc'd. for C$_{13}$H$_{18}$SO$_3$: C, 61.39; H, 7.30
Found: C, 60.98: H, 7.30

EXAMPLE 11

3-(4-cyclohexyl-1-oxobutyl)-4-hydroxy-2(5H)-furanone

To a solution of 1.0 g (10.0 mmol) of tetronic acid in 30 mL of dry N,N-dimethylformamide at 0° C. is added 1.5 mL (11 mmol) of triethylamine followed by 0.37 g (30 mmol) of 4 dimethylaminopyridine. After stirring at 0° C. for 5 minutes, 2.0 g (11.7 mmol) of 4-cyclohexyl butyric acid is added, followed by 2.25 g (11.7 mmol) of 1-(3-dimethylaminopropyl)-3-ethyl carbodiimide. After 10 minutes, the ice bath is removed and the reaction mixture is allowed to stir overnight. The reaction mixture is quenched with 1N HCl and the solution is washed three times with hexanes. The combined organic layers are washed with water, dried over magnesium sulfate and evaporated. The residue is flash chromatographed on silica gel using 5% methanol/ethyl acetate with 2 mL of acetic acid/liter to give an orange solid: m.p. 38– 42° C.; IR (film) 2920, 2840, 1770, 1690, 1660, 1600 cm$^{-1}$; NMR (CDCl$_3$) δ 0.9 (m, 2H), 1.2 (m, 6H), 1.7 (m, 6H), 2.9 (q, J=7 Hz, 2H), 4.6 and 4.7 (s, 2H), 12.1 (bs, 1H); MS (EI): M$^+$252.

Anal. Calc'd. for C$_{14}$H$_{20}$O$_4$: C, 66.64; H, 7.99
Found: C, 66.38; H, 7.90

EXAMPLE 12

3-(4-cyclohexyl-1-oxobutyl)4-hydroxy-2(5H)-thiophenone

The title compound is prepared in the same manner as that described for Example 11 with the exception that thiotetronic acid is used instead of tetronic acid. A tan solid is obtained: m.p. 45°–50° C.; IR (KBr): 2970, 2840, 1660, 1590 cm$^{-1}$; NMR (CDCl$_3$) δ 0.9 (m, 2H) 1.2 (m, 6H) 1.7 (m, 6H), 2.9 (t, J=7 Hz, 2H), 3.8 (s, 2H), 16.1 (bs, 1H); MS (EI) M$^+$ 268.

Anal. Calc'd. for C$_{14}$H$_{20}$O$_3$S: C, 62.66; H, 7.51
Found: C, 62.67; H, 7.53

EXAMPLE 13A

Cyclododecyl 3 allyl ether

To 2.6 g (54.3 mmol) of 50% sodium hydride that had been washed twice with hexanes was added 15 mL of N,N-dimethyl formamide followed by 10.0 g (5.4 mmol) of cyclododecanol. The reaction mixture was stirred at room temperature for several hours and then at 65° C. until the evolution of gas had ceased. 9.4 mL (108.5 mmol) of allyl bromide was then added and the reaction mixture was allowed to stir overnight at 65° C. The reaction was quenched with water, extracted 3 times with ether, the combined ether layers washed with water, dried over MgSO$_4$ and evaporated. The residue was flash chromatographed on silica gel using 2% Et$_2$O/Hexanes to give 5.34 g of an oil (44%).

EXAMPLE 13B

3(cyclododecyloxy)1,2 dihydroxy propane

To a mixture of cyclododecyl 3 allyl ether (5.0 g, 22.3 mmol) and 88% formic aced (26.3 mL) was added 3.12 g (24.5 mmol) of 30% hydrogen peroxide. The reaction mixture was heated to 40° C. and allowed to stir overnight. The excess formic acid and water was removed by rotary evaporation and the residue was refluxed for 1 h in 3N ethanolic potassium hydroxide. The ethanol was removed and the residue partitioned between ether and 1N HCl. The aqueous layer was washed with ether and the combined ether layers were dried over $MgSO_4$ and evaporated. The residue was flash chromatographed on silica gel using 70% ethyl acetate/hexanes to give 3.58 g of an oil (62%). NMR ($CDCl_3$): 3.4–3.8 ppm(m, 6H); 3.2 (bs, 2H); 1.4 (m,>10H).

EXAMPLE 13C

Cylododecyloxy acetic acid

To 1.9 g (7.4 mmol) of 3(cyclododecyloxy)1,2 dihydroxy propane in 20 mL of benzene was added 3.3 g (7.4 mmol) of lead tetraacetate and 2.0 g (14.8 mmol) of potassium carbonate. After stirring for several hours at room temperature, the reaction mixture was partitioned between ether and 1N HCl. The aqueous layer was washed with ether and the combined ether layers were dried over $MgSO_4$ and evaporated.

The crude residue was subjected to oxidation by Jones reagent in acetone at 0° C. The reaction mixture was again partitioned between ether and 1N HCl. The aqueous layer was washed with ether and the combined ether layers dried over $MgSO_4$ and evaporated. The residue was flash chromatographed on acidic silica gel using 10% EtOAc/Hexanes to give 0.7 g of a white solid (40%). IR (film): 2950, 2880, 1760, 1480 $cm^{-1}$; NMR ($CDCl_3$): 3.7 (s, 3H); 3.15 (s, 3H); 2.4 (t, 2H, J=8 Hz); 1.55 (q, 2H, J=6 Hz); 1.3 (m,>10H); MS(EI): $M^+$ 283.

|  |  | Theory | Found |
|---|---|---|---|
| Analysis: | % C | 72.03 | 71.13 |
|  | % H | 11.73 | 11.48 |
|  | % N | 4.94 | 4.17 |

EXAMPLE 13D

3-(2-cyclododecyloxyl-1-oxoethyl)-4-hydroxy-2(5H)-thiophenone

To a solution of 0.37 g (3.2 mmol) of thiotetronic acid in 20 mL of dry dichloromethane at 0° C. is added 0.4 mL (2.9 mmol) of triethylamine followed by 0.11 g (0.9 mmol) of 4-dimethylaminopyridine. After stirring at 0° C. for 5 minutes, 0.7 g (2.9 mmol) of cyclododecyloxyacetic acid is added, followed by 1.35 g (3.2 mmol) of 1-cyclohexyl-3-(2-morpholinoethyl) carbodiimide metho-p-toluene-sulfonate. After 10 minutes the ice bath is removed and the reaction mixture is allowed to stir overnight. The reaction mixture is quenched with 1N HCl. The layers are separated and the organic layer is washed twice with aqueous sodium bicarbonate and then twice with 2N HCl. The organic phase is then dried over $MgSO_4$ and the dichloromethane evaporated. The residue is flash chromatographed on acidic silica gel using 50% ether/hexanes and then recrystallized from hexanes to give a yellow solid: m.p. 93°–95° C.; IR (KBr) 2920, 2840, 1690, 1660, 1580 $cm^{-1}$; NMR (DMSO-d6) δ 1.2–1.6 (m, 10H), 3.4 (m, 1H), 3.95 and 4.4 (s, 2H), 4.6 (bs, 2H); MS (EI) $M^+$340.

Anal. Calc'd. for $C_{18}H_{22}O_4S$: C, 63.50; H, 8.29
Found: C, 63.30; H, 8.41

EXAMPLE 14

2-Cyclododecylethyl isocyanate

To 5.0 g of 3-cyclododecylpropionic acid (20.8 mmol) is 40 mL of toluene was added 7.6 mL (100 mmol) of thionyl chloride. The solution was refluxed overnight, stripped of solvent, taken up in toluene, and again stripped. The residue was taken up in toluene, subjected to the addition of 8.4 mL of trimethylsilyl azide (60 mmol), and heated to 100° C. until no further evolution of gas was observed. The reaction mixture was stripped of solvent and the crude product was used directly for the next reaction. Spectral data follow. $^1$H NMR ($CDCl_3$) δ 3.3 (triplet, 2H), 1.55 (t, 2H), 1.35 (bs,>20 H).

EXAMPLE 15

4-Hydroxy-2-oxo-2,5-dihydro-furan- 3-carboxylic acid-2-cyclododecyl-ethylamide To a dry flask containing 40 mL of chloroform was added 1.87 g (18.7 mmol) of tetronic acid, 2.29 g (18.7 mmol) of 4-N,N-dimethylaminopyridine, 2.6 mL (18.7 mmol) of triethylamine followed by 4.4 g (18.7 mmol) of 2-cyclododecylethyl isocyanate. The reaction mixture was allowed to stir overnight at room temperature, after which time a small amount of starting materials was still evident by TLC. The reaction mixture was quenched with 1N HCl, the layers separated, the organic fraction dried over $MgSO_4$, filtered, and stripped of solvent. The residue was flash chromatographed using acidic silica gel eluting with 25% EtOAc/hexane to give a yellow solid. M.P. 135°–137° C. Spectral data follow: 1H NMR (DMSO-$d_6$) δ 8.05 (bs, 1H), 4.6 (s, 2H), 4.2 (bs, 10 H), 3.25 (t, 2H), 2.5 (s, 3H), 1.2–1.4 (bm,>20 H); IR (KBr) 3340, 2920, 2850 (C-H), 1750, 1650 $cm^{-1}$ (C=O).

|  |  | Theory | Found |
|---|---|---|---|
| Analysis: | % C | 67.63 | 66.78 |
|  | % H | 9.26 | 8.89 |
|  | % N | 4.15 | 3.97 |

EXAMPLE 16A

Cyclododecylmethyl 3 allyl ether

To 2.4 g (50.4 mmol) of 50% sodium hydride that had been washed twice with hexanes was added 150 mL of N,N-dimethyl formamide followed by 10.0 g (50.4 mmol) of cyclododecyl methanol. The reaction mixture was stirred at room temperature for several hours and then at 65° C. until the evolution of gas had ceased. 8.7 mL (100.8 mmol) of allyl bromide was then added and the reaction mixture was allowed to stir overnight at 65° C. The reaction was quenched with water, extracted 3 times with ether, the combined ether layers was washed with water, dried over MgSO$_4$ and evaporated. The residue was flash chromatographed on silica gel using 2% Et$_2$O/Hexanes to give 5.5 g of an oil (49%). NMR(CDCl$_3$): 5.9 ppm (m, 1H); 5.2 (m, 2H); 3.95 (d, 2H, J=7 Hz); 3.25 (d, 2h, J=8 Hz); 1.3 (m,>10H).

EXAMPLE 16B

Cyclododecylmethoxy acetic acid

A solution of 4.5 g (20.1 mmol) of cyclododecylmethyl allyl ether in acetone at −78° C. was subjected to ozonolysis until the solution remained blue. The reaction mixture was quenched by the addition of 3.0 mL (40.2 mmol) of dimethyl sulfide. The volatiles were evaporated and the residue was subjected to Jones oxidation in acetone at )°C. The reaction mixture was partitioned between ether and 1N HCl. The aqueous layer was washed with ether and the combined ether layers were dried over MgSO$_4$ and evaporated. The residual material was recrystallized from hexanes to give 2.0 g of white solid (40%). NMR (CDCl$_3$): 4.0 ppm (s, 2H); 3.4 (d, 2H, J=7 Hz); 1.4 (m,>10H).

EXAMPLE 16C

According to the methods and reagents described above, 3-(cyclododecylmethoxy)acetyl]    -4-hydroxy-2(5H)-thiophenone was prepared as an off-white solid having a melting point of 93°–94° C.

EXAMPLE 17

The compounds of the invention are tested in an in vitro phospholipase A$_2$ assay to determine the ability of the compounds to inhibit the biosynthesis of platelet-activating factor and LTB$_4$ in purified human neutrophils.

This assay is carried out as follows:

Isolation of Human Polymorphonuclear Neutrophils:

A leukocyte enriched blood sample obtained from a healthy male donor is procured by leukophoresis using a Haemonetics model 30+ blood processor (Biological Specialties, Inc., Lansdale, Pa.). The top "platelet-rich" layer is removed after a low speed spin (35 xg, 15 min, 25° C.) of the sample. The remaining cell suspension is centrifuged (400 xg, 10 min, 25° C.) to sediment the remaining cells. The supernatant is discarded and the cell pellet resuspended in 120 ml HBSS (without Ca$^{++}$/Mg$^{++}$). The cell suspension is subjected to ficoll-hypaque sedimentation (Histopaque 1077, 400 xg, 30 min, 25° C). Contaminating erythrocytes are lysed by hypotonic shock (1 min). The cells are then washed once with 40 ml of HBSS and resuspended with HBSS (without Ca$^{++}$/Mg$^{++}$) to a concentration of 2.5×10$^7$ cells/ml for further use. Greater than 95% purity is obtained, as assessed by microscopic examination.

Platelet-Activating Factor Biosynthesis in Human Polymorphonuclear Neutrophils (PMN)

One ml of human PMN (2.5×10$^7$ cells/ml) is incubated with vehicle or drugs (10 µl) for 10 minutes at 30° C. After preincubation, an equal volume of HBSS (1 ml) containing 2.4 mM CaCl$_2$, 6 µM calcium ionophore A23187 and 50 µCi[$^3$H]-acetate is then incubated at 30° C. for 15 minutes. An aliquot (100 µl) of the reaction mixture is taken out and mixed with 900 µl of 15% ethanol. LTB$_4$ is extracted by using solid phase extraction on reverse phase C$_{18}$ columns to remove excess [$^3$H]-acetate and PAD. The C$_{18}$ column is prewashed once with 2 ml of ethanol and water. The sample aliquot is acidified with 0.1N HCl to pH 3 before applying to the column. The column is then washed with 2 ml of water followed by 2 ml of 15% ethanol and 2 ml of petroleum ether to remove excess labeled acetate. The sample is eluted with 2 ml of ethyl acetate. The collected samples are dried with nitrogen and resuspended in 0.5 ml RIA buffer. The quantity of LTB$_4$ in the sample is obtained from RIA determination. For PAF determination, the reaction is terminated by addition of 5 ml chloroform:methanol:acetic acid (2:1:0.04, v/v/v). [$^3$H]-PAF is obtained by Bligh and Dyer extraction. The chloroform phase is removed and dried under nitrogen. The residue is redissolved in 75 µl of chloroform:methanol (80:20, v/v). [$^3$H]-PAF is resolved from other phospholipids by TLC on RPC$_{18}$ plates with a solvent system of chloroform:methanol:water (2:3:1, v/v/v) and is quantitated using a Berthold automated TLC linear analyzer.

Data presented are the mean +/− s.d. of the values relative to control A23187 stimulated cells for each experiment assayed in triplicate. Percent inhibition when used is calculated as:

$$\% \text{ Inhibition}=100-[(x \div \text{Control})\times 100]$$

Dose response analysis is performed by non-linear regression analysis for curve fitting and IC$_{50}$ determination.

In this assay, scalaradial, an irreversible inhibitor of PLA$_2$, isolated from the marine sponge *Cacospongia sp.* gives an IC$_{50}$ of 1.0 µM.

When tested in this assay, the compounds of the invention gave the following results:

TABLE I

| Compound of Example No. | Dose, µM | % Inhibition PAF | Dose, µM | % Inhibition LTB$_4$ |
| --- | --- | --- | --- | --- |
| 1 | 10 | 84.3 | 10 | 95.1 |
| 2 | 10 | 79.2 | 10 | 69.6 |
| 3 | 10 | 64.4 | 10 | 90.4 |

EXAMPLE 18

The compounds of the invention are tested in an in vitro isolated phospholipase A$_2$ assay to determine the ability of the test compounds to inhibit the release of arachidonic acid from an arachidonic acid-containing substrate by the action of phospholipase A$_2$ enzyme from human and non-human sources.

This assay is carried out as follows:

Into a 15 mL polypropylene tube are added the following:

| Agent | Volume, µL | Final Conc. |
| --- | --- | --- |
| $^3$H-AA *E. coli* substrate[1] | 25 | 5 nmoles PL |
| CaCl$_2$ (0.1M)[2] | 5 | 5 mM |
| Tris-HCl (0.5M) pH 7.5[3] | 20 | 100 mM |
| Water[4] | 25 | |
| Drug/vehicle[5] | 1 | 50 µM |
| PLA$_2$ | 25 | Volume yielding 12% hydrolysis in 10 min. |

-continued

| Agent | Volume, µL | Final Conc. |
|---|---|---|
| | 100 | |

*pre-incubate at room temperature 30 min prior to substrate addition.
[1]Prepared by adding 2 mL deionized and distilled water to 2 mL $^3$H-arachidonate labeled E. coli (lower count), to which is added 1 mL of $^3$H-arachidonate labeled E. coli (higher count) to yield a total of 5 m substrate (containing 1000 nmoles phospholipid).
[2]Stock 0.1 m $CaCl_2$, required for enzyme activity.
[3]Stock 0.5 m Trisma-Base. Stock 0.5M Trisma-HCl. Adjust pH to 7.5 (optimum for enzyme).
[4]Deionized and distilled water.
[5]Stock 10 mM prepared in dimethyl sulfoxide. Make 1:2 dilution with dimethyl sulfoxide and add 1 µL to 100 µL assay tube.
[6]Two human $PLA_2$ enzymes are used:
a) Semi-purified human platelet acid extract $PLA_2$ (in 10 Mm sodium acetate buffer, pH 4.5). Remove protein precipitate by centrifugation at about 2200 rpm for 10 minutes.
b) Purified human synovial fluid.

Incubate the 100µL reaction mixture for 10 minutes at 37° C. in a shaking water bath. The reaction is terminated by the addition of 2 mL tetrahydrofuran, followed by vortexing. $NH_2$ columns (100 µg/mL—Analytichem International) are conditioned with 0.5 mL tetrahydrofuran followed by 0.5 mL tetrahydrofuran/water (2 mL:0.1 mL, v/v).

The sample is loaded onto the columns and slowly drawn through them. The hydrolyzed arachidonic acid retained in the columns is eluted therefrom with 1 mL tetrahydrofuran/ glacial acetic acid (2%). The arachidonic acid is transferred to scintillation vials and quantitated by β-counting analysis. A "total counts" sample is prepared by pipetting 25 µL $^3$H-arachidonate E.coli directly into a scintillation vial to which is added 1 mL tetrahydrofuran. 10 mL aquasol (scintillation cocktail) is added to all samples.

Calculations:

$$\% \text{ hydrolysis} = \frac{[3H]AA \text{ dpm (sample)} - [3H]AA \text{ dpm (nonspecific hydrolysis)}}{\text{total counts dpm}} \times 100$$

$$\% \text{ change} = \frac{\text{vehicle dpm} - \text{drug dpm}}{\text{vehicle dpm}} \times 100$$

Activity of Standard Drugs:

| | $IC_{50}$ (µM) | |
|---|---|---|
| Drug | Human Platelet $PLA_2$ | Human Synovial $PLA_2$ |
| Arachidonic Acid | 8.6 | 3.2 |
| Monoalide | 25.2 | 0.14 |

When tested in this assay, the compounds of the invention gave the following results:

TABLE II

| Compound of | % Inhibition at 10 µM | |
|---|---|---|
| Example No. | HP* | HSF** |
| 1 | −3.7 | 41.9 |
| 2 | 18.2 | 53 |

*human platelet
**human synovial fluid

EXAMPLE 19

The ability of the compounds of the invention to act as inhibitors of the enzymes 5-lipoxygenase and cyclooxygenase is measured in the resident murine peritoneal macrophage assay.

This assay is carried out as follows:

Resident peritoneal macrophages are collected from female Swiss Webster mice (49 days old, 20–25 gms, Buckshire) by lavaging with 7–8 ml Hanks Balanced Salt Solution (HBSS) without $Ca^{++}$ and $Mg^{++}$ (GIBCO). The lavage fluid from several mice is pooled and centrifuged at 4° C. for 10 minutes at 400 xg. The cell pellet is resuspended in Medium 199 (GIBCO) with HEPES buffer containing 100 µg/ml gentamicin. Two ml of the cell suspension ($4 \times 10^6$ cells) are then plated on 35 mm culture dishes (Nunc).

A macrophage monolayer is established after a 1–1.5 hour incubation of the cells at 37° C. in an atmosphere of 95% $O_2$ and 5% $CO_2$. The monolayers are washed 2x with 2 ml HBDSS, containing $Ca^{++}$ and $Mg^{++}$ after which 2 ml Medium 199 supplemented with 10% freshly thawed heat-inactivated fetal bovine serum and 100 µg/ml gentamicin is added for an overnight incubation.

Residual serum and cellular debris are removed from the monolayers by washing 3x with 2 ml HBSS containing $Ca^{++}$ and $Mg^{++}$. Macrophages are preincubated for 5 minutes with 1 ml serum-free M199 containing 10 µl dimethyl sulfoxide (DMSO) vehicle or test compound prior to cell activation with zymosan (100 Mg/ml) or arachidonic acid (AA) (2 µM). After 2 hours, the supernatants are removed and either assayed for $LTC_4$ and $PGE_2$ by radioimmunoassay (RIA) directly or stored at −20° C. In all cases, results are expressed as ng metabolite/$4 \times 10^6$ cells.

| Summary of RIAs used for quantitation of metabolite levels in zymosan or arachidonic acid stimulated mouse macrophage culture media. | | |
|---|---|---|
| Metabolite | Range of detection (µg/ml) | Metabolite Levels (ng/4 × 10$^6$ cells) (x ± S.E.M., n) |
| $LTC_4$ | 0.25–16 | 93.7 ± 9.9 (34) |
| $PGE_2$ | 0.027–20 | 30.90 ± 1.93 (39) |

Calculations

Raw data (dpm) may be stored directly onto an "Autostart" tape using the HP85 in room C-096. The raw data are converted to ng metabolite/$4$–$10^6$ cells using the standard curve by a "RIANAL" program (HP85) or a "NONLIN" program (HP9816). Results are then expressed as percent inhibition of zymosan induced, leukotriene or prostaglandin synthesis (control) using the equation:

% Inhibition =

$$\frac{\text{control metabolite level} - \text{sample metabolite level}}{\text{control metabolite level}} \times 100$$

REFERENCE COMPOUNDS

The compounds used are listed below.

$IC_{50}$ values of reference 5-lipoxygenase and/or cyclooxygenase inhibitors.

| Compound | IC$_{50}$ μM (95%) Confidence limit | |
|---|---|---|
| | LTC$_4$ | PGE$_2$ |
| BW 755c | 0.21 | 1.04 |
| | (0.10, 0.42) | (0.73, 1.49) |
| ETYA | 0.44 | 1.26 |
| | (0.36, 0.53) | (0.99, 1.60) |
| Indomethacin | >50 | 0.002 |
| | | (0.001, 0.003) |
| NDGA | 1.87 | 2.15 |
| | (0.22, 15.57) | (1.15, 4.04) |

When tested in this assay, the compounds of the invention exhibited the following levels of enzyme inhibition:

TABLE III

| Compound of | LTC$_4$ | | PGE$_2$ | |
|---|---|---|---|---|
| Example No. | Dose μM | % Inhibition | Dose μM | % Inhibition |
| 1 | 0.5 | 29.0 | 0.5 | 46.7 |
| 2 | 0.5 | 76.1 | 0.5 | 97.1 |
| 3 | 0.5 | 66.2 | 0.5 | 75.9 |
| 15 | 0.5 | 25.9 | 0.5 | 52.0 |
| 16 | 0.5 | 33.0 | 0.5 | 77.0 |

What is claimed is:

1. A compound having the formula

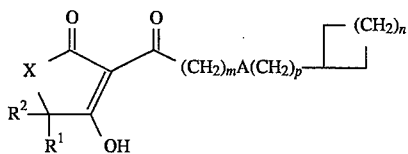

wherein

X is O;

R is hydrogen or lower alkyl;

R$^1$ and R$^2$ are each, independently, hydrogen, C$_{1-C10}$ alkyl, C$_{3-C20}$ cycloalkyl, phenylloweralkyl, or phenylloweralkyl substituted by halo, lower alkyl, lower alkoxy, halo lower alkyl, amino, monoloweralkylamino, diloweralkylamino or sulfonamido;

A is O, S, NR, or a chemical bond;

m is 0–15;

n is 3–12;

p is 0–15, where m+p=2–15;

and the pharmacologically acceptable salts thereof.

2. The compound of claim 1, having the name 3-(3-cyclododecyl-1-oxopropyl)-4-hydroxy-2(5H)-furanone or a pharmacologically acceptable salt thereof.

3. The compound of claim 1, having the name 3-(2-cyclododecyl-1-oxoethyl)-4-hydroxy-2(5H)-furanone or a pharmacologically acceptable salt thereof.

4. The compound of claim 1, having the name 3-(3-cyclohexyl-1-oxopropyl)-4-hydroxy-2(5H)-furanone or a pharmacologically acceptable salt thereof.

5. The compound of claim 1, having the name 3-(4-cyclohexyl-1-oxobutyl)-4-hydroxy-2(5H)-furanone or a pharmacologically acceptable salt thereof.

6. The compound of claim 1, having the name 4-hydroxo-2-oxo-2,5-dihydro-furan-3-carboxylic acid-2-cyclododecyl-ethylamide or a pharmacologically acceptable salt thereof.

7. A method for treating immunoinflammatory conditions in mammals which comprises administering to a mammal so afflicted an effective amount of a compound having the formula

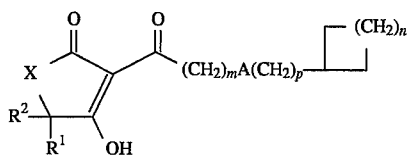

wherein

X is O;

R$^1$ and R$^2$ are each, independently, hydrogen, C$_1$-C$_{10}$ alkyl, C$_3$-C$_{20}$ cycloalkyl, phenylloweralkyl, or substituted phenylloweralkyl substituted by halo, lower alkyl, lower alkoxy, halo lower alkyl, amino, monoloweralkylamino, diloweralkylamino or sulfonamido;

A is O, S, NR or a chemical bond;

R, if present, is hydrogen or loweralkyl;

m is 0–15;

n is 0–20;

p is 0–15, where m+p≦15;

and the pharmacologically acceptable salts thereof.

8. The method of claim 7 wherein the compound is 3-(3-cyclododecyl-1-oxopropyl)-4-hydroxy-2(5H)-furanone or a pharmacologically acceptable salt thereof.

9. The method of claim 7 wherein the compound is 3-(2-cyclododecyl-1-oxoethyl)-4-hydroxy-2(5H)-furanone or a pharmacologically acceptable salt thereof.

10. The method of claim 7 wherein the compound is 3-(3-cyclohexyl-1-oxopropyl)-4-hydroxy-2(5H)-furanone or a pharmacologically acceptable salt thereof.

11. The method of claim 7 wherein the compound is 3-(4-cyclohexyl-1-oxobutyl)-4-hydroxy-2(5H)-furanone or a pharmacologically acceptable salt thereof.

12. The method of claim 7 wherein the compound is 4-hydroxo-2-oxo-2,5-dihydro-furan-3-carboxylic acid-2-cyclododecyl-ethylamide or a pharmacologically acceptable salt thereof.

* * * * *